US006657105B2

(12) United States Patent
Itohara et al.

(10) Patent No.: US 6,657,105 B2
(45) Date of Patent: Dec. 2, 2003

(54) PRION GENE MODIFIED MOUSE WHICH EXHIBITS HEART ANOMALIES

(75) Inventors: Shigeyoshi Itohara, Saitama (JP); Takashi Onodera, Ibaraki (JP); Hirokazu Tsubone, Ibaraki (JP)

(73) Assignee: Riken (JP)

( * ) Notice: Subject to any disclaimer, the term of this patent is extended or adjusted under 35 U.S.C. 154(b) by 0 days.

(21) Appl. No.: 09/768,319

(22) Filed: Jan. 25, 2001

(65) Prior Publication Data

US 2002/0004937 A1 Jan. 10, 2002

(30) Foreign Application Priority Data

Jan. 27, 2000 (JP) ........................................ 2000-019195

(51) Int. Cl.[7] ....................... A01K 67/027; A01K 67/00; G01N 33/00; C12N 15/63; C12N 15/87
(52) U.S. Cl. ................................. 800/18; 800/3; 800/8; 800/13; 800/21; 800/25; 435/455; 435/463; 435/325; 435/320.1
(58) Field of Search ................................. 800/3, 18, 21, 800/22, 25, 8, 13; 424/9.2; 435/4, 455, 463, 325, 320.1

(56) References Cited

U.S. PATENT DOCUMENTS

| 5,565,186 A | 10/1996 | Prusiner et al. ............... 424/9.2 |
| 6,008,435 A | 12/1999 | Prusiner et al. ................ 800/18 |

FOREIGN PATENT DOCUMENTS

| WO | WO 97/36477 | 10/1997 | .......... A01K/67/00 |
| WO | WO 98/13476 | 4/1998 | ............ C12N/5/00 |

OTHER PUBLICATIONS

Linder; The Influence of Genetic Background on Spontaneous and GeneticallymEngineered Mouse Models of Complex Diseases, 2001, Lab Animal, vol. 30: 34–39.*
Wall; Transgenic Livestock: Prgress and Prospects for the Future, 1996, Theriogenology 45: 57–68.*
T. Kitamoto et al., "Humanized Prion Protein Knock–in by Cre–Induced Site–Specific Recombination in the Mouse," *Biochem. Biophys. Res. Comm.*, 222: 742–47 (1996).
J.H. Miner et al., "Skeletal muscle phenotypes initiated by ectopic MyoD in transgenic mouse heart," *Development*, 114: 853–60 (1992).
J. Palermo et al., "Remodeling the mammalian heart using transgenics," *Cell. Mol. Biol. Res.*, 41(6): 501–9 (1995).
S. Tajbakhsh & D. Houzelstein, "In situ hybridization and β–galactosidase: A powerful combination for analyzing transgenic mice," *Trends in Genetics*, 11(2): 42.
J.G. Edwards et al., "Cardiomyopathy in Transgenic myf5 Mice," *Circ. Res.*, 78(3): 379–87, available at: http://circres.ahajournals.org/cgi/content/full/78/3/379.
European Search Report dated Sep. 6, 2002.

M. Poidinger et al., "Sequence Analysis of the PrP protein from two species of antelope susceptible to transmissible spongiform encephalopathy," *Arch. Virol.*, 131: 193–99 (1993).
A.R. Austin et al., "Abnormalities of the heart and rhythm in bovine spongiform encephalopathy," *Veterinary Record*, 141: 352–7 (1997).
S.B. Prusiner, "Transgenetic investigations of prion diseases of humans and animals," *Phil. Trans. R. Soc. Lond. B*, 339: 239–54 (1993).
C.J.L. Little et al., "Measurment of cardiac vagal tone in cattle: a possible aid to the diagnosis of BSE," *Veterinary Record*, 139: 527–28 (1996).
A.R. Austin et al., "Heart rate variability in BSE," *Veterinary Record*, 139: 631 (1996).
S.B. Prusiner, "Natural and experimental prion diseases of humans and animals," *Curr. Op. Neurobiol.*, 2: 638–47 (1992).
Hunter, N. et al., "Swaledale sheep affected by natural scrapie differ significantly in PrP genotype frequencies from healthy sheep and those selected for reduced incidence of scrapie," *J. Gen Vir.*, 74: 1025–31 (1993).
Oesch, B. et al., "A cellular gene encodes scrapie PrP 27–30 protein," *Cell*, 40: 735–46 (1995).
Scott, M.R. et al., "Compelling transgenic evidence for transmission of bovine spongiform encephalopathy prions to humans," *Proc. Natl. Acad. Sci. USA*, 96: 15137–42 (1999).
Telling, G.C. et al., "Transmission of Creutzfeldt–Jakob disease from humans to transgenic mice expressing chimeric human–mouse prion protein," *Proc. Natl. Acad. Sci. USA*, 91: 9936–40 (1994).
Westaway, D. et al., "Structure and polymorphism of the mouse prion protein gene," *Proc. Natl. Acad. Sci. USA*, 91: 6418–22 (1994).
Westaway, D. et al., "Homozygosity for prion protein alleles encoding glutamine–171 renders sheep susceptible to natural scrapie," *Genes Dev.*, 8: 959–69 (1994).
Prusiner, S.B., "Prions," *Proc. Natl. Acad. Sci. USA*, 95: 13363–83 (1998).

(List continued on next page.)

*Primary Examiner*—Deborah Crouch
*Assistant Examiner*—Thai-An N. Ton
(74) *Attorney, Agent, or Firm*—Finnegan, Henderson, Farabow, Garrett & Dunner, L.L.P.

(57) ABSTRACT

The present invention relates to a method for detecting an aberrant animal-derived prion gene wherein the method comprises steps of introducing a prion gene of an animal into a mouse to produce a prion gene modified mouse and determining that the prion gene is aberrant when the prion gene modified mouse exhibits heart anomalies; a prion gene modified mouse which exhibits heart anomalies; and a method for detecting drugs which reduce abnormal waves in an electrocardiogram of the mouse.

17 Claims, 9 Drawing Sheets

OTHER PUBLICATIONS

Bronson, S.K. et al., "Single–copy transgenic mice with chosen–site integration," *Proc. Natl. Acad. Sci. USA*, 93: 9067–72 (1996).

Yokoyama, T. et al., "In vivo conversion of cellular prion protein to pathogenic isoforms, as monitored by conformation–specific antibodies," *J. Biol. Chem.*, 276: 11265–71 (2001).

Onodera, T. et al., "Isolation of scrapie agent from the placenta of sheep with natural scrapie in Japan," *Microbiol. Immunol.*, 37(4): 311–16 (1993).

Szabo, A. et al., "Further characterization of forebrain serotonin receptors mediating tachycardia in conscious rats," *Brain Res. Bull.*, 45: 583 Abstract (1998).

Manoach, M. et al., "The role of catecholamines on intercellular coupling, myocardial cell synchronization and self ventricular defibrillation," *Mol. Cell. Biochem.*, 147: 181 Abstract (1995).

Tisdale, J.E. et al., "Electrophysiologic and proarrhythmic effects of intravenous inotropic agents," *Prog. Cardiovasc. Dis.*, 38: 167 Abstract (1995).

Inoue, H., "Drug–induced arrhythmias," *Nippon Rinsho*, 54: 2220 Abstract (1996).

Janse, M.J., "Electrophysiology of arrhythmias," *Arch. Mal. Coeur Viass.*, 92 (Spec. No. 1): 9 Abstract (1999).

\* cited by examiner

```
                1                                                              50
sheep      MVKSHIGSWI LVLFVAMWSD VGLCKKRPKP GGGWNTGGSR YPGQGSPGGN
oryx       .......... .......... .......... .......... ..........
mouflon    .......... .......... .......... .......... ..........
takin      .......... .......... .......... .......... ..........

100
sheep      RYPPQGGGGW GQPHGGGWGQ PHGGGWGQPH GGGWGQPHGG GGWGQGGSHS
oryx       .......... .......... .......... .......... .......T..
mouflon    .......... .......... .......... .......... ..........
takin      .......... .......... .......... .......... ..........

150
sheep      QWNKPSKPKT NMKHVAGAAA AGAVVGGLGG YMLGSAMSRP LIHFGNDYED
oryx       .......... .......... .......... .......... ..........
mouflon    .......... .......... .......... .......... ..........
takin      .......... .......... .......... .......... .....S....

200
sheep      RYYRENMYRY PNQVYYRPVD QYSNQNNFVH DCVNITVKQH TVTTTTKGEN
oryx       .......... .......... .......... .......... ..........
mouflon    .......... .......... .......... .......... ..........
takin      .......... .......... .......... .......... ..........

250
sheep      FTETDIKIME RVVEQMCITQ YQRESQAYYQ RGASVILFSS PPVILLISFL
oryx       .......... .......... .......... .......... ..........
mouflon    .......... .......... .......... .......... ..........
takin      .......... .......... .......... .......... ..........

256
sheep      IFLIVG*
oryx       .......
mouflon    .......
takin      .......
```

*FIG. 2*

```
              1                                                   50
sheep         ATGGTGAAAA GCCACATAGG CAGTTGGATC CTGGTTCTCT TTGTGGCCAT
oryx          .......... .......... .......... .......... ..........
mouflon A     .......... .......... .......... .......... ..........
mouflon B     .......... .......... .......... .......... ..........
takin         .......... .......... .......... .......... ..........

100
sheep         GTGGAGTGAC GTGGGCCTCT GCAAGAAGCG ACCAAAACCT GGCGGAGGAT
oryx          .......... .......... .......... .......... ..T.......
mouflon A     .......... .......... .......... .......... ..........
mouflon B     .......... .......... .......... .......... ..........
takin         .......... .......... .......... .......... ..........

150
sheep         GGAACACTGG GGGGAGCCGA TACCCGGGAC AGGGCAGTCC TGGAGGCAAC
oryx          .......... ...A...... .......... .......... ..........
mouflon A     .......... .......... .......... .......... ..........
mouflon B     .......... .......... .......... .......... ..........
takin         .......... .......... .......... .......... ..........

200
sheep         CGCTATCCAC CTCAGGGAGG GGGTGGCTGG GGTCAGCCCC ATGGAGGTGG
oryx          .......... .......... .......... .......... ..........
mouflon A     .......... .......... .......... .......... ..........
mouflon B     .......... .......... .......... .......... ..........
takin         .......... .......... .......... .......... ..........

250
sheep         CTGGGGCCAA CCTCATGGAG GTGGCTGGGG TCAGCCCCAT GGTGGTGGCT
oryx          .......... .......... .......... .......... ..........
mouflon A     .......... .......... .......... .......... ..........
mouflon B     .......... .......... .......... .......... ..........
takin         .......... .......... .......... .......... ..........

300
sheep         GGGGACAGCC ACATGGTGGT GGAGGCTGGG GTCAAGGTGG TAGCCACAGT
oryx          .......... .......... .......... .......... ..C.......
mouflon A     .......... .......... .......... .......... ..........
mouflon B     .......... .......... .......... .......... ..........
takin         .......... .......... .......... .......... ..........

350
sheep         CAGTGGAACA AGCCCAGTAA GCCAAAAACC AACATGAAGC ATGTGGCAGG
oryx          .......... .......... .......... .......... ..........
mouflon A     .......... .......... .......... .......... ..........
mouflon B     .......... .......... .......... .......... ..........
takin         .......... .......... .......... .......... ..........

400
sheep         AGCTGCTGCA GCTGGAGCAG TGGTAGGGGG CCTTGGTGGC TACATGCTGG
oryx          .......... .......... .......... ......A... ..........
mouflon A     .......... .......... .......... .......... ..........
mouflon B     .......... .......... .......... .......... ..........
takin         .......... .......... .......... .......... ..........
```

(CONTINUED)

```
                                                                              450
sheep       GAAGTGCCAT GAGCAGGCCT CTTATACATT TTGGCAATGA CTATGAGGAC
oryx        ....C..... .......... .......... .......... ..........
mouflon A   .......... .......... .......... .......... ..........
mouflon B   .......... .......... .......... .......... ..........
takin       .......... .......... .......... ......G... ..........

500
sheep       CGTTACTATC GTGAAAACAT GTACCGTTAC CCCAACCAAG TGTACTACAG
oryx        ........C. .......... .......... .......... ..........
mouflon A   .......... .......... .......... .......... ..........
mouflon B   .......... .......... .......... .......... ..........
takin       .......... .......... .......... .......... ..........

550
sheep       ACCAGTGGAT CAGTATAGTA ACCAGAACAA CTTTGTGCAT GACTGTGTCA
oryx        .......... .......... .......... .......... ..........
mouflon A   .......... .......... .......... .......... ..........
mouflon B   .......... .......... .......... .......... ..........
takin       .......... .......... .......... .......... ..........

600
sheep       ACATCACAGT CAAGCAACAC ACAGTCACCA CCACCACCAA GGGGGAGAAC
oryx        .......... .......... .......... .......... ..........
mouflon A   .......... .......... .......... .......... ..........
mouflon B   .......... .......... .......... .......... ..........
takin       .......... .......... .......... .......... ..........

650
sheep       TTCACCGAAA CTGACATCAA GATAATGGAG CGAGTGGTGG AGCAAATGTG
oryx        .......... .......... ...C...... .......... ..........
mouflon A   .......... .......... .......... .......... ..........
mouflon B   .......... .......... .......... .......... ..........
takin       ......T... .......... .......... .......... ..........

700
sheep       CATCACCCAG TACCAGAGAG AATCCCAGGC TTATTACCAA AGGGGGGCAA
oryx        .......... .......... .......... .......... ..A.......
mouflon A   .......... .......... .......... .......... ..........
mouflon B   .......... .......... .......... .......... ....C.....
takin       .......... .......... .......... .......... ..........

750
sheep       GTGTGATCCT CTTTTCTTCC CCTCCTGTGA TCCTCCTCAT CTCTTTCCTC
oryx        .......... ...C...... .......... .......... ..........
mouflon A   .......... .......... .......... .......... ..........
mouflon B   .......... G......... .......... .......... ..........
takin       .......... .......... .......... .......... ..........

770
sheep       ATTTTTCTCA TAGTAGGATA G
oryx        .......... .......... .
mouflon A   .......... .......... .
mouflon B   .......... .......... .
takin       .......... .......... .
```

FIG. 3

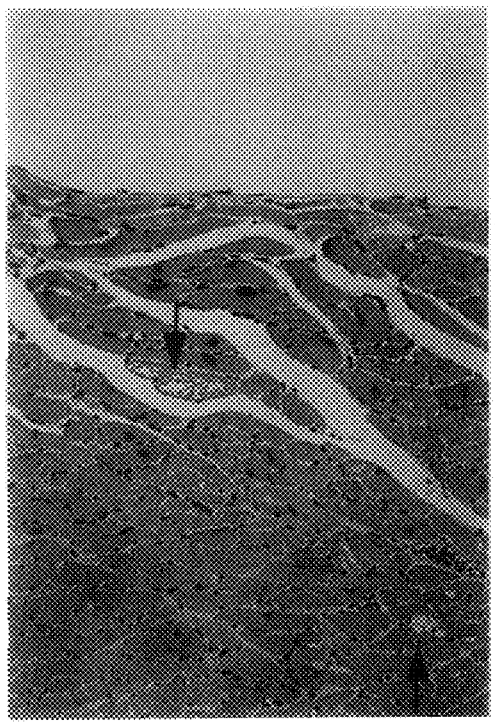 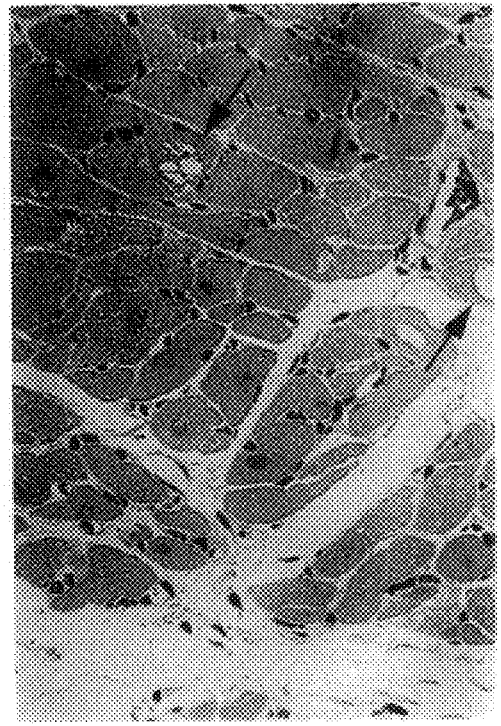
(a) VACUOLAR DEGENERATION OF MYOCARDIAL CELL
(b) SMALL GRANULE FORMATION IN MYOCARDIAL CYTOPLASM
*FIG. 7(a)*
*FIG. 7(b)*

(C) CICATRIZATION IN MYOCARDIAL TISSUE

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:primer P(16)

<400> SEQUENCE: 1
gcgggatcca tggcgaacct tggctac                               27

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:primer P(17)

<400> SEQUENCE: 2
gcgggatcct catcccacga tcaggaaga                             29

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:primer used
      to confirm the presence of neomycin resistant gene.

<400> SEQUENCE: 3
cgcatcgcct tctatc                                           16

<210> SEQ ID NO 4
<211> LENGTH: 22
<212> TYPE: DNA
<213> ORGANISM: Artificial Sequence
<220> FEATURE:

```
<223> OTHER INFORMATION: Description of Artificial Sequence:primer
      P(103)

<400> SEQUENCE: 4
tttgttgcct tcaatcggct at                                          22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: forward
      primer used for PrP gene cloning.

<400> SEQUENCE: 5
gggcatttga tgctgacacc                                             20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: reverse
      primer used for PrP gene cloning.

<400> SEQUENCE: 6
gaagaattag aaacggtcca ac                                          22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: forward
      primer used for PCR.

<400> SEQUENCE: 7
ggttgttgtg ctgtctcatc a                                           21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: reverse
      primer used for PCR.

<400> SEQUENCE: 8
tcgctccatg atcttgatgt cagt                                        24
```

PRION GENE MODIFIED MOUSE WHICH EXHIBITS HEART ANOMALIES

FIELD OF THE INVENTION

The present invention relates to a method for detecting an aberrant animal-derived prion gene. The invention further relates to a prion gene modified mouse which exhibits heart anomalies, and to a method for detecting drugs which reduce anomalies in an electrocardiogram of said mouse.

PRIOR ART

Transmissible spongiform encephalopathy is a neurodegenerative disease observed in many kinds of mammal. These diseases are prion diseases caused by anomalies in prion proteins (PrP). Among these, kuru, Creutzfeldt-Jacob disease (CJD), Gerstmann-Straussler-Scheinker desease (GSS) in humans; and scrapie and bovine spongiform encephalopathy in ruminant livestocks such as sheep and cattle are known, and are a serious problems even today. A cause of the epidemic of prion diseases such as BSE in animals is thought to be livestock feed from sheep infected with scrapie, however, the causal link between the feed and incidence has not been confirmed.

The British medical journal "Lancet" issued on Apr. 6, 1996 reported 10 cases of human transmissible spongiform encephalopathy, a new type of Creutzfeldt-Jacob disease (CJD) in the United Kingdom. This disease has been on the increase having killed 48 persons in the United Kingdom and 2 persons in France; and CJD has been under surveillance all over the world including Japan. The World Health Organization (WHO) has promoted research and development using transgenic animals. They are considered to be useful for detecting diseases sensitively in early stages and developing removal methods of pathogens. Owing to this research, the causal link between mad cow disease and CJD is gradually being elucidated.

At present, in Prusiner's report (S. Prusiner et al. PNAS 96:15137–15192, 1999) a bovine prion gene modified mouse is presented; and each pathogen, BSE, scrapie and CJD is said to appear at around 200 days in this transgenic mouse. Accordingly, the transgenic mouse indicates the high possibility that these three pathogens are identical. On the other hand, in Collinge's report (J. Collinge et al. PNAS, 91:9936–9940, 1994), a human prion gene modified mouse was presented; and CJD is said to appear at around 220 days in this mouse. However, a mouse in which the incubation period has been shortened using various animal-derived prion genes, is not yet known.

It is of great interest to note the fact that a wild ruminant such as kudu and oryx has a shorter incubation period compared with that of livestock ruminants such as sheep and cattle; and their progress after incidence is rapid. For example, it has been reported that generally the incubation period in sheep is 36–48 months and incidence is at age 36–48 months, and in cattle the incubation period is 36–72 months and the incidence is at age 60–80 months, but on the other hand, in Oryx demmah the incubation period is 21 months and incidence is at age 30 months. This indicates that the difference of transmissibility of spongiform encephalopathy and the incubation period might depend on the difference of amino acid sequence of each PrP. Up to now, the gene encoding a prion protein has been identified in many mammals such as human, sheep, cattle, mouse, hamster, etc; and it is known that their genes show not less than 90% amino acid homology to each other and they are highly conserved (N. Oesch et al., Cell, 40, 735 (1985); D. Westaway et al., Proc. Nat. Acad. Sci. USA 91: 6418–6422 (1994); D. Westaway et al., Genes and Develop. 8:959–969 (1994); N. Hunter et al., J. Gen. Virol. 74 1025–1031 (1993)).

Now the system for rapidly detecting the scrapie pathogen is required to be established. Human or bovine prion gene modified transgenic mice have not yet been provided sufficiently in the world; therefore under present circumstances, the pathogen is detected by inoculating the animal tissues of interest in the brain of an ordinary CD-1 mouse (CLEA JAPAN). In the case of inoculating sheep brain tissue with this method, at least 300 days are required for the detection. Establishing a method for detecting the aberrant prion gene within a shortened incubation period before prion disease incidence may overcome the disadvantage of detection by the present bioassay which has high sensitivity but lacks rapidness.

On the other hand, a heart disease model in mouse is rare. Although the transgenic mouse with familial amyloid polyneuropathy has been reported, there is no report of a transgenic mouse as a heart specific disease model. The prion gene modified mouse with heart specific disease may also be useful for developing pharmaceuticals for heart diseases and studies on life-style related diseases.

The object of the present invention is to provide a method for detecting an aberrant animal-derived prion gene.

The present inventors have studied extensively and intensively to solve the above problems and have now found that a prion gene modified mouse exhibits heart disease when a foreign prion gene is aberrant, thereby completing the invention.

Furthermore, in the past, there was no report which confirms abnormal electrocardiogram wave profiles and abnormal tissues in the heart of a mouse which overexpresses mouse normal prion genes (m-Prnp) (*Prion and Prion Disease,* Jun Tateishi. KYORITSU SHUPPAN, p23 (1998)).

SUMMARY OF THE INVENTION

The present invention relates to a method for detecting an aberrant animal-derived prion gene in which the prion gene is determined to be aberrant when the prion gene modified mouse exhibits heart disease.

The invention further relates to a prion gene modified mouse which exhibits heart disease.

Still further, the invention relates to a method for detecting drugs which reduce abnormal waves in an electrocardiogram of the prion gene modified mouse.

The invention will be described in detail as follows.

BRIEF DESCRIPTION OF THE DRAWINGS

FIG. 2 shows the comparison between the amino acid sequences of prion proteins in sheep, Oryx demmah, Mouflon and Takin.

FIG. 3 shows the comparison between prion gene translated regions of sheep, Oryx demmah, Mouflon (A and B) and Takin.

DETAILED DESCRIPTION OF THE INVENTION

Figure 1:
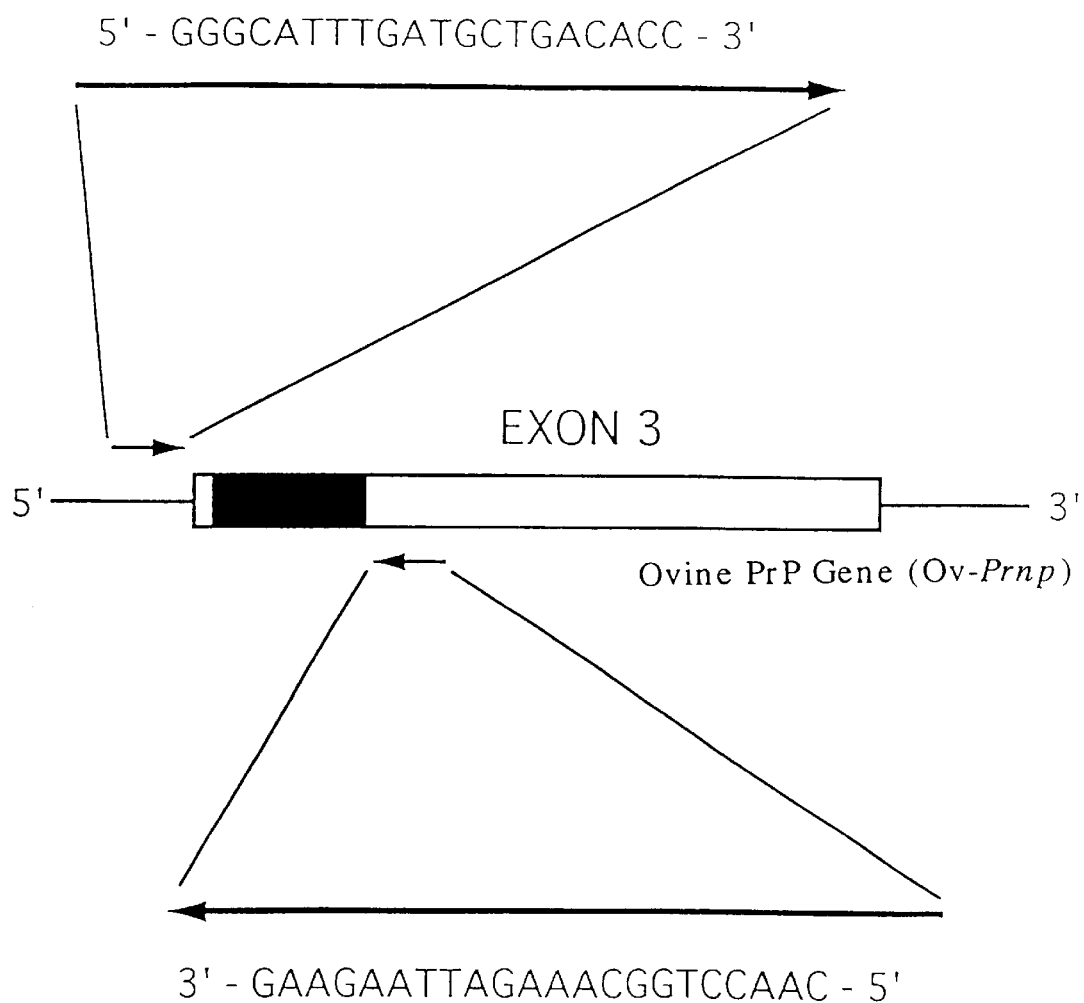
FIG. 1 shows primers used for cloning Oryx demmah prion gene.
Figure 4:
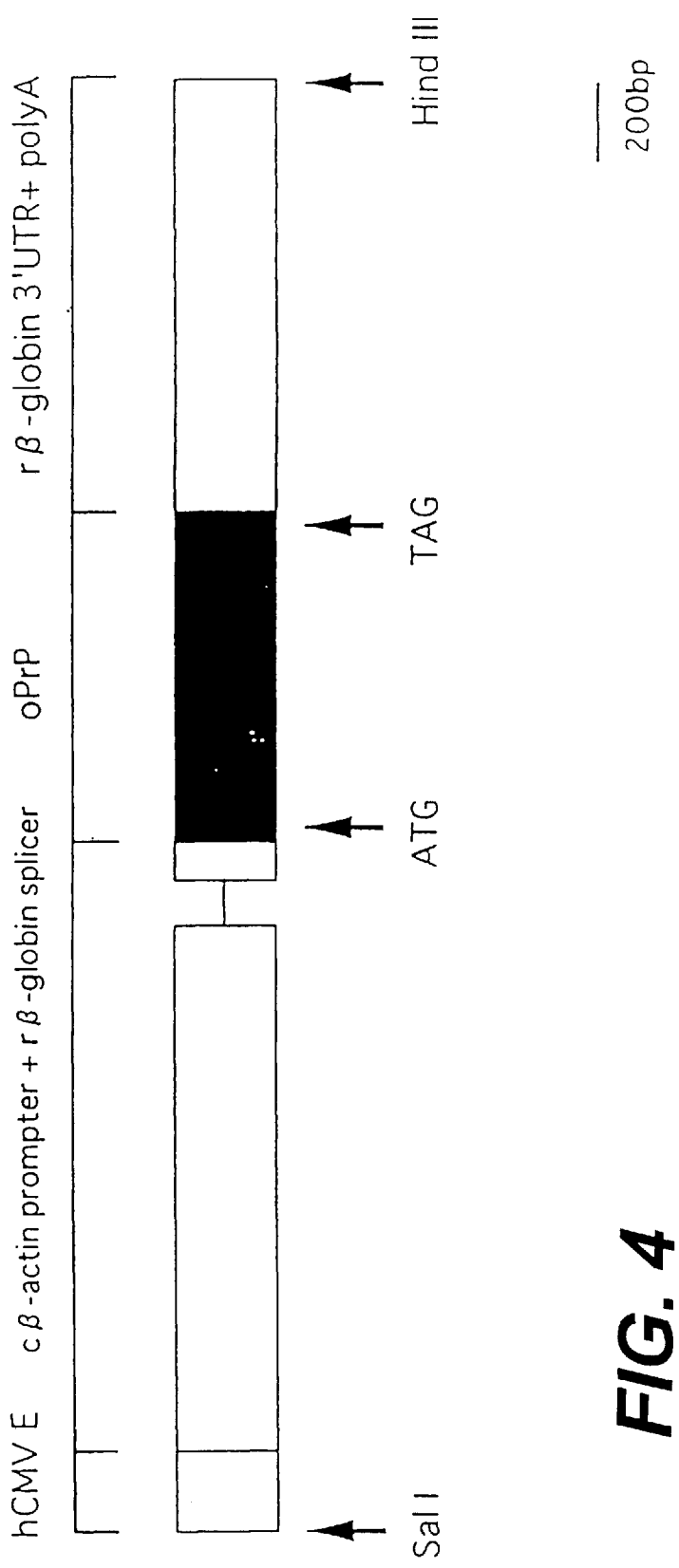
FIG. 4 shows the DNA cassette used to prepare transgenic mice.
Figure 5:
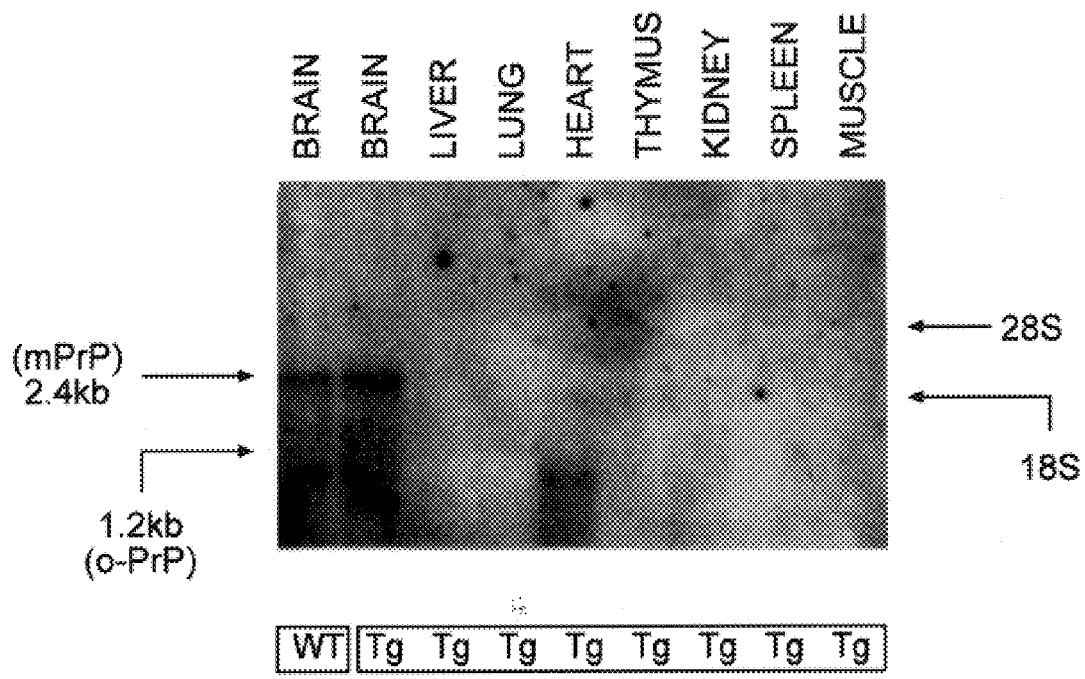
FIG. 5 shows RNA expression in each organ of Or-Prnp transgenic mice as confirmed by Northern Blot.

The present invention relates to a method for detecting an aberrant animal-derived prion gene in which the prion gene is determined to be aberrant when the prion gene modified mouse exhibits heart disease.

As used herein, the term "aberrant prion gene" means the prion gene which shows symptoms of prion diseases in organs such as brain and heart when being expressed within a native organism.

The detection of an aberrant animal-derived prion gene can be carried out as follows for example.

1. Production of Prion Gene Knockout Mice

At first, the open reading frame (ORF) and neighboring regions of mouse prion gene were cloned, followed by insertion or substitution of a drug resistant gene as a marker gene into the ORF portion, or deletion of this portion in the usual manner known in the art to inactivate the prion gene (i.e. gene disruption).

Subsequently, the inactive gene is substituted for an active gene on a chromosome according to the method for transferring DNA into an animal known in the art to obtain chimera mice. Among the resulting chimera mice, a heterozygote (+/−) which has a substituted (disrupted) targeting gene on the one chromosome is selected; and these heterozygous mice are crossed to obtain prion gene knockout mice having disrupted prion genes on both chromosomes (for further information, see R. Brinster et al., Proc. Natl. Acad. Sci. USA, 82: 4438–4442 (1985); C. Stewart et al., EMBO J. 6: 383–388 (1987); A. Bradley et al., Nature 309: 255–256 (1984); H. Bueler et al., Cell 73: 1339–1347 (1993); S. Sakaguchi et al., Nature 380:528–531 (1996)).

The drug resistant gene used as a marker gene includes, but is not limited to, neomycin (neo) resistant gene and gancyclovir (ganc) resistant gene.

The method for transferring DNA into an animal known in the art includes, but is not limited to, microinjection, viral vector, and Embryonic stem cell methods.

2) Transferring an Animal-derived Prion Gene (Foreign Prion Gene) of Interest

Next, the open reading frame (ORF) of the prion gene extracted from muscular tissues from the animal of interest is incorporated into a DNA cassette under the control of actin promoter in the usual method known in the art to prepare a plasmid vector.

The plasmid vector is introduced into a fertilized egg of a normal (non-knockout) mouse in the usual method (e.g. microinjection) to allow the egg to develop, thereby obtaining a first-stage transgenic mouse. This transgenic mouse is further crossed with the prion gene knockout mouse produced in 1) above to obtain a second-stage transgenic mouse.

The tail of the resulting second-stage transgenic mouse is partially cut to prepare DNA; and PCR is performed using the DNA to obtain a prion gene modified mouse having only foreign prion genes.

The animal from which the foreign prion gene to be transferred into a prion gene knockout mouse is derived, can be any kind of animals including, but not limited to, human, cattle, sheep, mouse, rat, hamster, mink, antelope, chimpanzee, gorilla, rhesus monkey, marmoset and squirrel monkey.

A preferable mouse to which an animal-derived prion gene is transferred is the prion gene knockout mouse produced as in 1) above, but a normal mouse can also be used.

3) Determination of an Aberrant Prion Gene

Subsequently, the foreign prion gene prepared as in 2) which is transferred into a prion gene modified mouse is determined as to whether it is aberrant or not.

Said determination can be performed, for example, by observing the presence of myocardial diseases in the prion gene modified mouse.

When the mouse is young, a heart stimulant is administered and if abnormal waves in electrocardiogram are observed (i.e. the state in which the QRS wave becomes biphasic while it is normally monophasic), said foreign prion gene is determined to be aberrant.

In the case of an aged mouse, when abnormal waves in electrocardiogram and myocardial disease-affected heart tissues are observed, said foreign prion gene is determined to be aberrant.

In the present invention, it is required that a prion gene transferred from an animal is fully expressed in the cardiac muscle of a transgenic mouse by genetic engineering techniques. This is confirmed by extracting RNA from cardiac muscle in the mouse and confirming a positive band by Northern blotting using the animal-derived prion gene of interest as a probe.

The heart stimulant includes, but is not limited to, atropine, epinephrine, serotonin, dopamine and catecholamines.

The invention further relates to a prion gene modified mouse with heart disease.

The mouse is thought to be useful in the development and safety testing of cardiac pharmaceuticals for humans and animals having underlying heart diseases and life-style diseases. It is also thought to be useful for detecting drugs which reduce abnormal waves in an electrocardiogram of said mouse.

EXAMPLE

The present invention will be described more in detail by means of examples, but it is not intended that the invention is limited to these.

Example 1

Preparation of a Mouse having an Oryx Demmah Prion Gene

1) Preparation of a Prion Gene Knockout Mouse

DNA was extracted from the thymus of a C57BL/6 mouse; then a prion gene was isolated by PCR and its structure was clarified by dideoxytermination. The primers used were P(16): 5'-GCGGGATCCATGGCGAACCTTGGCTAC-3' (SEQ ID NO:1) and P(17): 5'-GCGGGATCCTCATCCCACGATCAGGAAGA-3' (SEQ ID NO:2). A 785 bp band was obtained by PCR. This band portion was dissolved with prep-A-Gene DNA purification matrix and it was used as a cloning sample. The fragment was introduced into a plasmid by using QIAGEN plasmid kit (Funakoshi, Tokyo) to amplify genes in *E. coli*. The amplified genes were sequenced by using ABI PRISM 3110 gene analysis system (Perkin-Elmer, Chiba, Japan). Furthermore, genomic DNA clone was obtained from 129/SV-derived phage library (Clontech). The phage DNA was extracted from phage particles purified by cesium chloride density-gradient centrifugation in the usual method.

Subsequently, by using the DNA, a targeting vector was prepared in which the ORF portion was substituted by a neomycin (neo) resistant gene connected to pgk-1 promoter. This targeting vector was introduced into an embryonic stem cell (ES cell) derived from a 129/ola mouse, by electroporation (800V, 3 μF: Gene Pulser from BIO-RAD) to obtain a transformant with the indication of a marker (neo resistance gene). In the case where neo was used, a cell colony which resists to the drug G418 was selected.

Then, the transformant was cultured in ES cell medium (Boehringer Mannheim, Tokyo); and from this culture, cells in which homologous recombination occurred were identified by Southern hybridization.

An ES cell having a selected substituted target gene was injected into the blastocyst collected from a mouse to prepare a chimeric embryo.

The chimeric embryo was implanted into the uterus of a foster mouse and allowed to develop to breed chimeric mice. Whether the mice have a targeting gene substituted by the neo resistance gene was determined by Southern hybridization using DNA prepared by excising a part of the tail.

The probe used is a 3'-side SacI-SacI 350 bp fragment of m-Prnp gene. The genomic DNA was digested at BamHI. By this operation, a 9 kb band from the wild type gene and 5kb band from the targeting gene were detected respectively.

The presence of neomycin resistant gene can also be confirmed by PCR. For this purpose, the following primer (5'-CGCATCGCCTTCTATC-3': SEQ ID NO:3) was used. This primer is a part of the resistant gene sequence. Furthermore, a partial sequence of the prion gene, P(103): 5'-TTTGTTGCCTTCAATCGGCTAT-3' (SEQ ID NO:4), which is thought to be included in the 5'-terminal (upstream) of the resistant gene was used as another primer.

35 cycles of PCR were performed in which each cycle was carried out under the conditions of 2 min at 95° C. (denaturation), 1.5 min at 60° C. (annealing), 1 min at 72° C. (extension). After performing 30 cycles, extension was lengthened to 7 min at 72° C. 50 μL reaction mixture contained 5 μL DNA, 50 pmol of each primer, 0.2 mM dNTP, 50 mM KCl, 10 mM Tris-HCl (pH 8.3), 1.5 mM MgCl$_2$ and 0.5 unit Taq polymerase.

The PCR products were run on 1.5% agarose gel electrophoresis, resulting in detection of an approximately 1269 bp band under ultraviolet irradiation.

Some pups were heterozygotes (+/−) having a disrupted gene on the one chromosome. These mice were further crossed, resulting in the production of homozygotes (−/+) having disrupted prion genes on both chromosomes, that is, prion gene knockout mice.

2) Introduction of Oryx Demmah Prion Gene (Or-Prnp)

Figure 6:
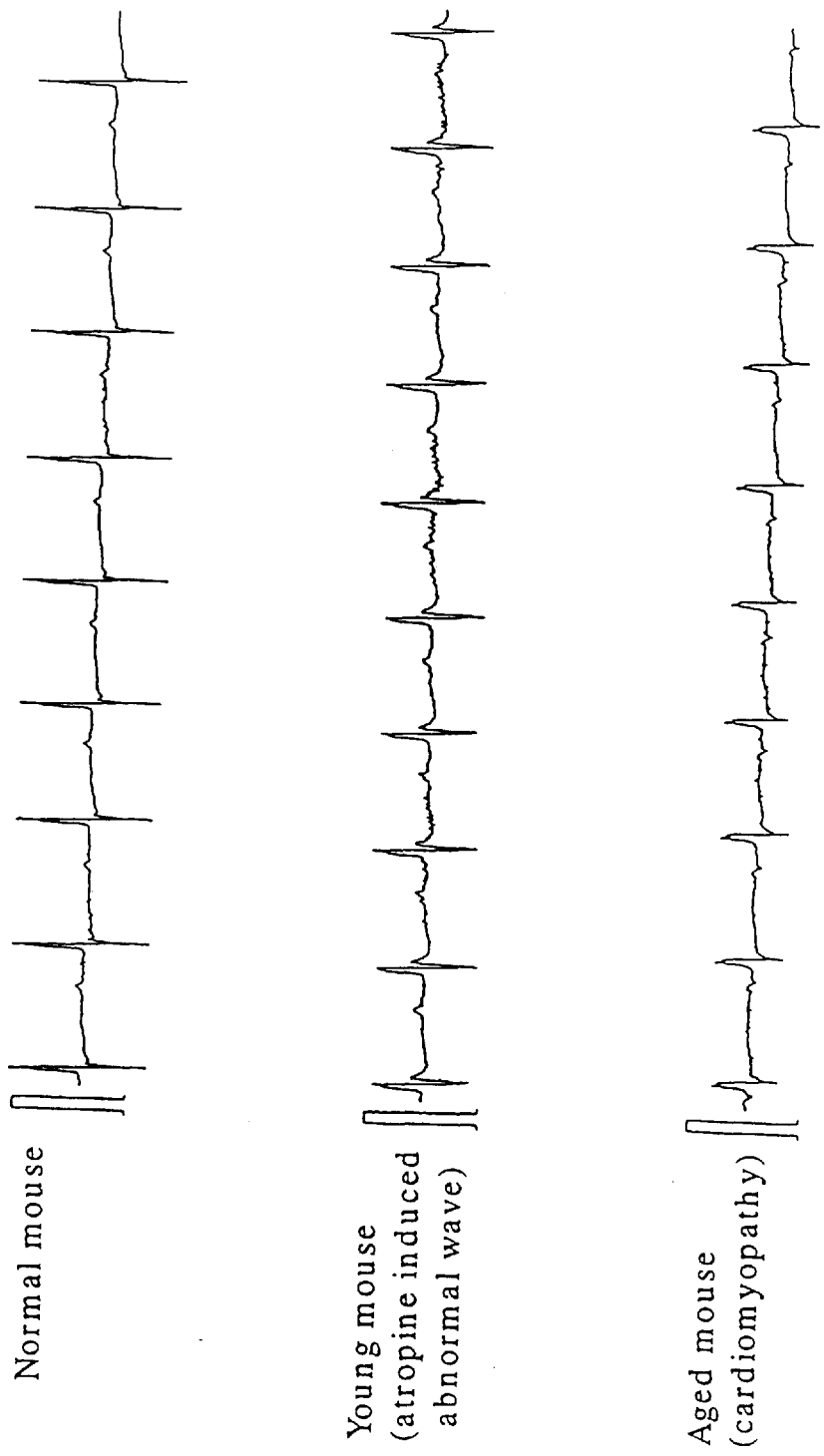
FIG. 6 shows the electrocardiogram of Oryx prion gene modified mice and a normal mouse.

DNA was extracted from muscular tissues of Oryx demmah (male, 10 years-old); and for the purpose of cloning PrP gene, two types of primers (forward primers: 5'-GGGCATTTGATGCTGACACC-3' (SEQ ID NO:5), reverse primers 3'-GAAGAATTAGAAACGGTCCAAC-5' (SEQ ID NO:6)) were designed from sheep PrP gene which has been already reported. By using these primers, DNA-PCR was performed and the resulting DNA fragment was cloned. The fragment was inserted into a plasmid by using QIAGEN plasmid kit (Funakoshi, Tokyo) to amplify the genes in *E. coli.* The amplified genes were sequenced with ABI PRISM 3110 gene analysis system (Perkin-Elmer, Chiba). The PCR conditions used were as follows.

To a 400 μg DNA sample, 50 pmol of both primers (forward primers: 5'-GGTTGTTGTGCTGTCTCATCA-3' (SEQ ID NO:7), reverse primers: 5'-TCGCTCCATGATCTTGATGTCAGT-3' (SEQ ID NO:8)), 0.5 unit Taq DNA polymerase (Perkin-Elmer, Chiba), 25 mM $MgCl_2$, 100 mM Tris-HCl (pH 8.3), 500 mM KCl and 10 mM dNTPs were added to give a total amount of 50 μL.

35 cycles of PCR were performed by using Gene Amp PCR system model 2400 (Perkin-Elmer). Each cycle was carried out under the conditions of 1.5 min at 95° C. (denaturation), 1.5 min at 58° C. (annealing) and 1 min at 72° C. (extension).

The PCR products were run on 1.5% agarose gel electrophoresis, resulting in detection of an approximately 860-bp band under ultraviolet irradiation. This band was dissolved with Prep-A-Gene DNA purification matrix (BIO-RAD, Richmond, Calif.) to use as a cloning sample.

Subsequently, for the purpose of preparing Or-Prnp transgenic mice which express Or-Prnp in each organ, an Or-Prnp gene of translated region was particularly incorporated under the control of an actin promoter. The synthesized gene was introduced into a fertilized egg of a C57BL/6 mouse by microinjection to obtain progeny.

Four lines of Or-Prnp transgenic mice were established. Using DNA prepared from tails of these mice, the presence of Or-Prnp was confirmed by Southern blot.

Furthermore, the detection of Or-Prnp mRNA was attempted in each organ in all mice of 4 lines. Extraction of RNA from tissues was performed with a TRISOL agent (GIBCO, Tokyo). A tissue/TRISOL mixture was adjusted to give an amount of 50–100 mg/mL and homogenized. Then, 0.2 equivalent chloroform was added, and followed by centrifugation at 10,000 g for 30 min at 4° C.; and the mixture was separated into an oil layer and a water layer. The water layer was transferred to a different test tube, followed by addition of equivalent isopropanol to precipitate RNA. After precipitation for 1 hour at −20° C., centrifugation was performed at 10,000 g for 20 min at 4° C. to collect RNA. The collected pellet was washed twice with 70% ethanol and preserved in RNAase-free distilled water.

For the purpose of RT-PCR, 1 μg RNA was dissolved in 20 μL mixture containing 10 mM Tris-HCl (pH 8.3), 5 mM $MgCl_2$, 50 mM KCl, 4 mM dNTPs, 50 units Molony leukemia virus-derived reverse transcriptase (US BIO CHEMICALS, Greenland, Ohio) and 2.5 M oligo d(T) primers.

To the resulting cDNA, 50 pmol of both detector primers (forward primers: 5'-GGTTGTTGTGCTGTCTCATCA-3' (SEQ ID NO:7), reverse primers: 5'-TCGCTCCATGATCTTGATGTCAGT-3' (SEQ ID NO:8) were added to perform PCR. RT-PCR was performed under the conditions of 100 μL mixture containing 10 mM Tris-HCl (pH 8.3), 50 mM KCl, 50 pmol of both detector primers (aforedescribed) and 0.5 unit Taq polymerase (Stratagene, La Jolla, Calif.). 35 cycles were performed and each cycle was carried out under the conditions of 1.5 min at 60° C. (annealing), 2 min at 72° C. (extension) and 1.5 min at 95° C. (denaturation).

Or-Prnp transgenic mice and prion gene defective (KO) mice prepared as in 1) were crossed to obtain a pup. Then, by using the pup, the same operation was performed.

In each organ of some mice tested by RT-PCR, Or-Prnp mRNA expression was confirmed. Expression was highly observed in the heart and bands were slightly seen in the brain, kidney and muscle, indicating that the expression rate is organ dependent (data not shown). Furthermore, confirmation by Northern blot showed the strong RNA expression in the heart (FIG. 5).

The strong expression of Or-Prnp mRNA in the heart indicates the mass production of Oryx demmah PrP in the heart; and for the purpose of examining the effect, the electrocardiogram of mice was observed.

Results

Concerning the electrocardiogram of an Or-Prnp transgenic mouse over 50 weeks-old, an abnormal QRS wave was observed. The electrocardiogram compared to that of a normal mouse is shown in FIG. 6. At this time 30 transgenic mice, aged 50 wks old, were tested for electrocardiogram. Fourteen mice showed abnormal QRS wave.

Figure 7C:
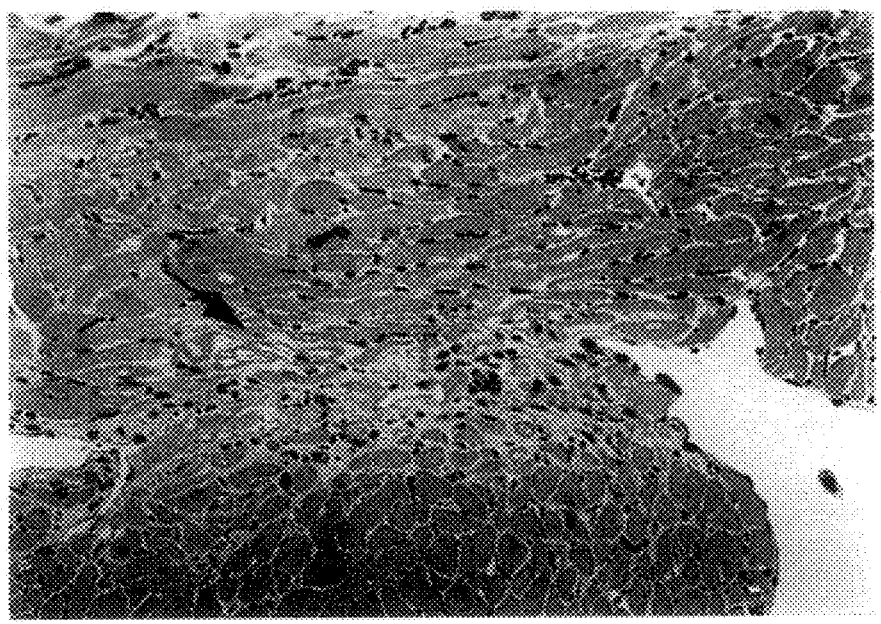
FIG. 7 shows the diseases in cardiac muscle tissues in a mouse which exhibits abnormal waves in an electrocardiogram.

Concerning the mouse showing the abnormal QRS wave, pathological/histological examinations were performed in the brain and heart, resulting in disease formation in some parts of the brain and cardiac muscle. In cardiac muscle, vacuolar degeneration of muscle cell, increase of tissue-binding tissues and ventricular diastole were observed. Observational results are shown in FIG. 7. 10 mice were tested for histopathology. All of 50 wks old transgenic mice showed vacuolation in heart muscle. In these mice having myocardial diseases, degenerative diseases were observed also in some parts of brain tissues (hippocampus) and foot muscle (data not shown).

Example 2

Induction of Abnormal Waves in Electrocardiogram by Heart Stimulant

Among Or-Prnp transgenic mice prepared in Example 1, the electrocardiograms of 9–10 weeks-old mice do not differ greatly from those of wild mice of the same age. However, due to intra-abdominal administration of a heart stimulant, atropine in low concentration (4 mg/kg) with physiological saline, only Or-Prnp transgenic mice showed the abnormal waves in electrocardiogram. The results compared to those of normal mice are shown in FIG. 6 along with the results of Example 1.

According to the results of Example 1 and 2, it was confirmed that prion gene modified mouse into which the aberrant prion gene had been transferred showed the abnormal QRS waves in electrocardiogram, by drug administration in young mice and spontaneously in older mice.

Consequently, this prion gene modified mouse enables detection of drugs which reduce abnormal waves in electrocardiogram.

Effect of the Invention

The present invention provides a method for detecting an aberrant animal-derived prion gene. The invention further provides a prion gene modified mouse with heart disease. The mouse is considered to be useful for development and safety testing of cardiac pharmaceuticals for human and animals having underlying diseases or life-style related diseases and detecting drugs for reducing abnormal waves in electrocardiogram in said mouse.

What is claimed is:

1. A transgenic mouse whose genome comprises a transgene, said transgene comprising a heterologous prion gene operatively linked to a promoter, wherein the mouse develops heart anomalies.

2. The mouse according to claim 1, wherein the promoter controls expression of the transgene in heart tissue.

3. The mouse according to claim 2, wherein the promoter is an actin promoter.

4. The animal-derived mouse according to claim 1, wherein the heterologous animal-derived prion gene is an Oryx demmah prion gene.

5. The mouse according to claim 4, wherein the mouse exhibits an abnormal electrocardiogram due to drug administration.

6. The mouse according to claim 5, wherein the abnormal electrocardiogram is a biphasic QRS wave.

7. The mouse according to claim 5, wherein the drug is one or more of atropine, epinephrine, serotonin, dopamine, and a catecholamine.

8. The prion gene modified mouse according to claim 7, wherein the drug is atropine.

9. The mouse according to claim 1, wherein the mouse exhibits an abnormal electrocardiogram due to drug administration.

10. The mouse according to claim 9, wherein the abnormal electrocardiogram is a biphasic QRS wave.

11. The mouse according to claim 9, wherein the drug is one or more of atropine, epinephrine, serotonin, dopamine, and a catecholamine.

12. The mouse according to claim 11, wherein the drug is atropine.

13. A method for detecting drugs which reduce abnormal waves in an electrocardiogram of the mouse according to claim 5, comprising administering the drug to the mouse of claim 5, and determining if the drug reduces the abnormal waves in the electrocardiogram.

14. A method for detecting drugs which reduce abnormal waves in an electrocardiogram of the mouse according to claim 9, comprising administering the drug to the mouse of claim 9, and determining if the drug reduces the abnormal waves in the electrocardiogram.

15. A method of producing a transgenic mouse whose genome comprises a transgene comprising a heterologous prion gene operatively linked to a promoter, wherein the mouse develops heart anomalies, the method comprising:

a) introducing a transgene comprising a prion gene operatively linked to a promoter into a fertilized egg or an embryo of a mouse, b) transferring the egg or embryo comprising the transgene to a surrogate mother mouse; and c) allowing the transferred egg or embryo comprising the heterologous prion transgene to develop to produce a transgenic mouse whose genome comprises a transgene comprising a heterologous prion gene operatively linked to a promoter, wherein the mouse develops heart anomalies.

16. The method according to claim 15, wherein the promoter controls expression of the transgene in heart tissue.

17. The method according to claim 16, wherein the promoter is an actin promoter.

* * * * *

UNITED STATES PATENT AND TRADEMARK OFFICE
CERTIFICATE OF CORRECTION

PATENT NO. : 6,657,105 B2
DATED : December 2, 2003
INVENTOR(S) : Shigeyoshi Itohara et al.

It is certified that error appears in the above-identified patent and that said Letters Patent is hereby corrected as shown below:

Column 9,
Line 60, "The animal-derived mouse" should read -- The mouse --.
Line 61, "heterologous animal-derived prion" should read -- heterologous prion --.

Column 10,
Line 55, "The prion gene modified mouse" should read -- The mouse --.

Column 11,
Line 2, "claim 5, and" should read -- claim 5; and --.
Line 7, "claim 9, and" should read -- claim 9; and --.

Signed and Sealed this

Twenty-third Day of March, 2004

JON W. DUDAS
*Acting Director of the United States Patent and Trademark Office*